United States Patent [19] [11] 4,138,418
Warning et al. [45] Feb. 6, 1979

[54] PROCESS FOR THE PREPARATION OF ω,ω-DIALKOXYCARBOXYLIC ACID DERIVATIVES

[75] Inventors: Klaus Warning, Liederbach; Michael Mitzlaff, Bad Homburg, both of Fed. Rep. of Germany

[73] Assignee: Hoechst Aktiengesellschaft, Frankfurt am Main, Fed. Rep. of Germany

[21] Appl. No.: 883,940

[22] Filed: Mar. 6, 1978

[30] Foreign Application Priority Data

Mar. 8, 1977 [DE] Fed. Rep. of Germany ....... 2709995

[51] Int. Cl.$^2$ ............................ C11C 3/02; C09F 5/00
[52] U.S. Cl. .............................. 260/410.9 R; 260/404; 260/561 B; 560/186
[58] Field of Search ......... 260/404, 410.9 R, 410.9 Q, 260/410.9 L, 561 B; 560/186

[56] References Cited

U.S. PATENT DOCUMENTS 3,535,351  10/1970  Dorfman et al. .................... 260/404

OTHER PUBLICATIONS

Manly et al. Chem. Absts., vol. 51: 3549f.
Lukes et al., Chem. Absts., vol. 50, No. 7795.
Tsyhina et al., Chem. Absts., vol. 79, No. 5204k.

Primary Examiner—John Niebling
Attorney, Agent, or Firm—Curtis, Morris & Safford

[57] ABSTRACT

ω,ω-Dialkoxycarboxylic acid derivatives I (amides and esters) are prepared by heating ω-alkoxylactams II with hydrogen halide in an alcohol. When using only a catalytical quantity of hydrogen halide, there are obtained the amides, when using a quantity of hydrogen halide which is at least about equimolar, there are obtained the esters of the corresponding ω,ω-dialkoxycarboxylic acids. Since the compounds I are acetals, they may be readily converted into the corresponding ω-formyl compounds. Both the acetals I and the corresponding ω-formyl compounds are valuable intermediates for the synthesis of for example prostaglandins, sexual attractants and antioxidants.

4 Claims, No Drawings

PROCESS FOR THE PREPARATION OF ω,ω-DIALKOXYCARBOXYLIC ACID DERIVATIVES

The present invention relates to a process for the preparation of ω,ω-dialkoxycarboxylic acid derivatives.

ω-Formylcarboxylic acid derivatives, ω-formylcarboxylic acid amides and esters and moreover the acetals derived therefrom are valuable intermediates, for example for the synthesis of prostaglandins (S. B. Thakur et al., Indian J. Chem. 12, (1974), 893, ref. in Chem. Inform 1975, 4–192; I. T. Harrison et al., Tetrahedron Letters 1972, 5151, D. Taub et al., Tetrahedron 29, 1447 (1973)), of sexual attractants (U.S. Pat. Nos. 3,852,419, 3,845,108; W. Roelofs et al., Science 174 (1971) 4006, 297) and of antioxidants (G.B. Pat. No. 1.396.875).

The hitherto known processes for the preparation of these classes of compounds are unsatisfactory in various regards.

Thus, the desired azelaic semialdehyde is obtained only in 5.4% yield upon ozonolysis of the technical-grade oleic acid (cf. Z. Prikl. Chim. 43 (1970), 3, 627 ref. in Chem-Inform 1970, 25–108), and the ω-formylvaleric acid is obtained in 35% yield upon ozonolytic ring opening of cyclohexene (V. N. Odinokov et al., Zh. Org. Khim. 9, 671 (1973)).

The process comprising an oxidative ring cleavage of acyloins with lead tetraacetate (J. R. Hazon, J. Org.-Chem. 35, 973 (1970)) has the disadvantages that the latter compound is very expensive and that the corresponding acyloin must frequently be prepared in complicated manner.

The proposed ring-opening oxidation of cyclic enol ethers using hydrogen peroxide in the presence of boron or of a compound of metals of the fifth or sixth side chain of the periodic table (cf. German Offenlegungsschrift No. 2,252,780) gives the desired compounds in a yield of less than 50% only, and moreover the occurring by-products make a fractionation of the reaction mixture necessary.

The present invention, consequently, was confronted with the problem of developing a more economical process for the preparation of ω-formylcarboxylic acid derivatives, especially of the ω-formylcarboxylic acid amides and esters and/or of the corresponding acetals, which are ω,ω-dialkoxycarboxylic acid derivatives.

This problem could be solved in simple manner by finding a process in which ω-alkoxylactams are heated with hydrogen halide in an alcohol.

The present invention, consequently, provides a process for the preparation of ω,ω-dialkoxycarboxylic acid derivatives of the formula

(RO)$_2$CH(C$_n$H$_{2n}$)—COX    (I)

in which
R is a primary or secondary, preferably a primary, alkyl radical having of from 1 to 4 carbon atoms,
n is an integer of from 2 to 10 and
X is the NH$_2$ or an OR group with R having the above meaning, which comprises converting ω-alkoxylactams of the formula

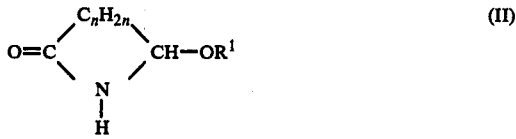

in which R$^1$ has the same meaning as R in the formula I and n has the same meaning as n in the formula I,
into ω,ω-dialkoxycarboxylic acid derivatives of the formula I with X being NH$_2$ (these compounds being ω,ω-dialkoxycarboxylic acid amides) by heating them with a catalytical quantity of hydrogen halide in an alcohol ROH with R having the same meaning as in the formula I, and optionally further reacting the compounds obtained by further heating them with a quantity of hydrogen halide which is at least about equimolar in the same alcohol ROH to yield ω,ω-dialkoxycarboxylic acid derivatives of the formula X with X being OR (these compounds being, consequently, ω,ω-dialkoxycarboxylic acid esters).

The starting product in the process of the invention are ω-alkoxylactams of the formula II, in which the (C$_n$H$_{2n}$) groups may be linear or branched, preferably linear, alkyl groups.

Suitable starting compounds are, for example, 5-methoxypyrrolidone-2, 6-ethoxypiperidone-2, 7-n-butoxy-ε-caprolactam, 7-i-propoxy-ε-caprolactam and ω-methoxylaurinolactam. These ω-alkoxylactams may be prepared from the corresponding unsubstituted lactams by electrochemical alkoxylation according to the processes disclosed in German patent applications DOS Nos. 2,557,765 and P 26 053 089.2. In these processes the unsubstituted lactams are alkoxylated anodically with an alcohol R$^1$OH in the presence of at least one alkali metal tetrafluoroborate or tetraalkylammonium tetrafluoroborate, -hexafluorophosphate or -nitrate as the conducting salt, at a temperature of up to about 100° C., in an electrolysis cell containing a stationary or flowing electrolyte. The quantity of current preferably applied is in the range of from about 2 to 3.5 Faradays per mol of starting lactam, preferred conducting salts of the alkali metal and/or tetraalkylammonium tetrafluoroborates, especially the sodium tetrafluoroborate, the potassium tetrafluoroborate and the tetramethylammonium tetrafluoroborate. The most suitable concentration of conducting salt is in the range of from about 0.01 to 2.0 mols/liter, the preferred electrolysis temperature is in the range of from about 0 to 60° C. and the preferred molar ratio between starting lactam and alcohol is in the range of from about 1:2 to 1:100.

The process according to the invention is preferably carried out in the following manner: The ω-alkoxylactam employed in each case of the formula II is dissolved in the alcohol ROH, to the solution formed is added a catalytical quantity of hydrogen halide and the mixture is kept at the reaction temperature until completion of the ring opening process, which may be easily observed by sampling and by chromatograhic analysis of the samples. The quantity of the solvent (alcohol) is not critical. Preferably, however, an excess of solvent, calculated on the ω-alkoxylactam, which is in the range of from about 2 to 50 mols, preferably of from about 5 to 30 mols and especially of from about 10 to 20 mols, per mol of ω-alkoxylactam II, is used. Greater quantities are possible, but do not bring about any advantage.

The term "catalytical quantity" of hydrogen halide means to understand a small quantity which is commonly used for catalysts. This quantity may be in the range of from about 0.5 to 10 mol %, preferably of from about 1 to 3 mol %, calculated on the ω-alkoxylactam II. When using greater quantities, there are obtained increasing quantities of ester corresponding to the formula I with X being OR, in addition to the corresponding ω,ω-dialkoxycarboxylic acid amide of the formula I with X being $NH_2$.

Suitable hydrogen halides are hydrogen fluoride, hydrogen chloride, hydrogen bromide or hydrogen iodide, hydrogen chloride being employed preferably.

The required reaction temperatures may vary in the range of from about +20° to 120° C. and are preferably in the range of from about 60° to 90° C. The reaction is preferably performed at reflux temperature of the alcohol ROH. A preferred alcohol ROH is that in which the alkyl radical R is the same as the alkyl radical $R^1$ in the starting lactam II. A particularly preferred radical $R^1$ is that which corresponds to R and which denotes $CH_3$.

The preferred reaction periods are in the range of from about 3 to 10 hours.

The reaction times are the shorter, the greater the employed quantity of hydrogen halide and the higher the reaction temperatures and the longer, the lower the quantity of hydrogen halide and the reaction temperatures.

If desired, the ω,ω-dialkoxycarboxylic acid amides of the formula I with X being $NH_2$, which have been obtained using a catalytical quantity of hydrogen halide, may be easily converted into the corresponding esters of the formula I with X being OH, according to the process of the invention. For this purpose, said amides must be further heated with a quantity of hydrogen halide, which is at least about equimolar, calculated on the ω,ω-dialkoxycarboxylic acid amide, in the same alcohol ROH. If this further reaction is desired, the ω,ω-dialkoxycarboxylic acid amide first obtained need not be isolated from its alcoholic solution, but it remains in this solution and is reacted to give the desired ester suitably by simply adding or introducing further quantities of hydrogen halide and by heating. The reactions according to the invention take place according to the following equations:

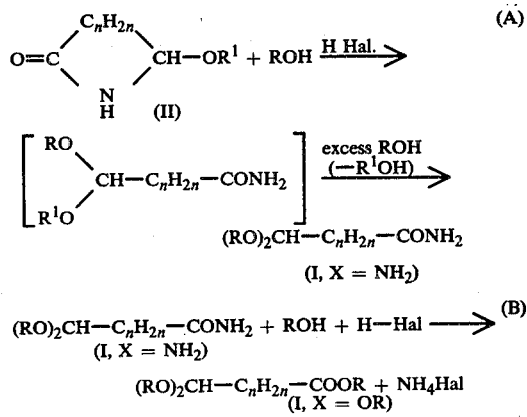

According to a preferred variant of the process of the invention both reaction steps A and B may be combined in one step by directly reacting the ω-alkoxylactams of the formula II in the alcohol ROH to give ω,ω-dialkoxycarboxylic acid esters of the formula I with X being OR by heating them with a quantity of hydrogen halide which is at least about equimolar. The reaction conditions are the same as those which have been hereinbefore mentioned.

For treating purposes, the reaction batches are neutralized, for example with sodium hydroxide, potassium hydroxide or with sodium alcoholate, and are subsequently distilled in vacuo, whereupon the ω,ω-dialkoxycarboxylic acid derivatives of the formula I are obtained as colorless liquids or as crystalline compounds.

Since these compounds are the acetals of the corresponding ω-formylcarboxylic acid derivatives, the free formyl compounds may be prepared therefrom, if desired, by a gentle treatment in an acidic medium, for example using an acidic ion exchanger, without affecting the amide or ester function.

The following examples illustrate the invention:

EXAMPLE 1

A solution of 14.3 g (0.1 mol) of 7-methoxy-ε-caprolactam in 100 ml of methanol is refluxed with 1 ml of a 6N methanolic hydrochloric acid for 6 hours. Upon neutralization with sodium methylate solution and filtration, the mixture is distilled in vacuo. There are obtained 13.1 g (74.9% of the theory) of 6,6-dimethoxycaproic acid amide having a boiling point under 0.02 bar of 120° C. and a melting point of 57° C. (from diisopropyl ether)

analysis: $C_8H_{17}NO_3$: calc.: C, 54.9%; H, 9.7%; N, 8.0%; O, 27.4%. found: C, 54.9%; H, 9.2%; N, 8.0%; O, 27.4%.

EXAMPLE 2

12.9 g (0.1 mol) of 5-ethoxypyrrolidone-2 are dissolved in 100 ml of ethanol and 0.15 mol of gaseous hydrogen chloride is added thereto. The batch is refluxed for 6 hours, suction-filtered from the precipitated ammonium chloride, neutralized with a solution of sodium ethylate in ethanol and distilled in vacuo. There are obtained 10.5 g (51.5% of the theory) of 4,4-diethoxybutyric acid ethyl ester having a boiling point under 0.05 bar of 48° C. The $n_D^{20}$ is 1.4227.

analysis: $C_{10}H_{20}O_4$: calc.: C, 58.9%; H, 9.8%; O, 31.3%. found: C, 58.8%; H, 9.7%; O, 31.4%.

EXAMPLE 3

25.8 g (0.2 mol) of 6-methoxypiperidone-2 are refluxed for 4 hours with 120 ml of a methanolic hydrochloric acid containing 0.3 mol of HCl. The precipitated ammonium chloride is removed by suction-filtration, the reaction mixture is neutralized with a solution of sodium methylate in methanol and distilled in vacuo. There are obtained 21 g (59.7% of the theory) of 5,5-dimethoxyvaleric acid methyl ester having a boiling point under 0.01 bar of 34° C. The $n_D^{20}$ (found) is 1.4213. The boiling point under 2.3 bars is in the range of from 70° to 72° C., the $n_D^{26}$ is 1.4206 (according to J. R. Hazen, J. Org. Chem. 35, 973 (1970)).

NMR (CDCl$_3$): 1.5–1.8 (m, 2 CH$_2$); 2.2–2.5 (m, CH$_2$); 3.3 (s, 2 OCH$_3$); 3.7 (s, COOCH$_3$), 4.4 (m, CH)

EXAMPLE 4

A solution of 17.1 g (0.1 mol) of 6-n-butoxypiperidone-2 in 100 ml of n-butanol is saturated with gaseous HCl and is stirred for 8 hours at 60° C. Subsequently the mixture is neutralized with a solution of sodium butylate in butanol, suction-filtered from the precipitated ammonium chloride and is distilled in vacuo.

There are obtained 14.3 g (47.4% of the theory) of 5,5-di-n-butoxy-valeric acid n-butyl ester having a boiling point under 0.05 bar of 120° C. and a $n_D^{20}$ of 1.4351.

analysis: $C_{17}H_{34}O_4$: calc.: C, 67.5%; H, 11.3%; O, 21.2%. found: C, 67.0%; H, 10.9%; O, 22.0%.

EXAMPLE 5

A solution of 28.6 g (0.2 mol) of 7-methoxy-ε-caprolactam is refluxed with 100 ml of a methanolic hydrochloric acid containing 0.4 mol of HCl. Upon neutralization with a solution of sodium methylate in methanol, suction-filtration of the precipitated salt and distillation in vacuo there are obtained 26.2 g (68.9% of the theory) of 6,6-dimethoxycaproic acid methyl ester having a boiling point (found) under 0.2 bar of 72° C. and a $n_D^{20}$ (found) of 1.4260. The boiling point under 2.2 bars is 83° C. and the $n_D^{26}$ 1.4262 (according to C. D. Hurd and W. H. Saunders jr., J.Am.Chem.Soc. 74, 5324 (1952)).

NMR(CDCl$_3$): 1.2–2.0 (m, 3 CH$_2$); 2.1–2.5 (m, CH$_2$); 3.35 (s, 2 OCH$_3$); 3.7 (s, COOCH$_3$); 4.2–4.5 (CH)

EXAMPLE 6

A solution of 22.7 g (0.1 mol) of ω-methoxylaurinolactam is refluxed for 6 hours with 100 ml of a methanolic hydrochloric acid containing 0.2 mol of HCl. Upon neutralization with a solution of sodium methylate in methanol, filtration of the precipitated salt and distillation in vacuo there are obtained 14.0 g (51.0% of the theory) of ω,ω-dimethoxylauric acid methyl ester having a boiling point under 0.05 bar of 120° C.

analysis: $C_{15}H_{30}O_4$: calc.: C, 65.6%; H, 11.0%; O, 23.4%. found: C, 64.7%; H, 10.6%, O, 24.3%.

What is claimed is:

1. A process for the preparation of ω,ω-dialkoxycarboxylic acid derivatives of the formula

in which
R is a primary or secondary, preferably a primary, $C_{1-4}$ alkyl radical,
n is an integer of from 2 to 10,
X is the NH$_2$ or OR group, wherein R is defined as above which comprises converting ω-alkoxylactams of the formula

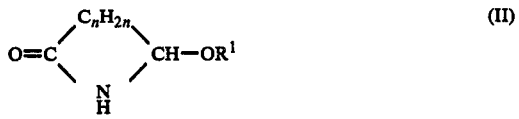

in which $R^1$ is a primary or secondary, preferably a primary, $C_{1-4}$ alkyl radical and
n is defined as in formula I,
into ω,ω-dialkoxycarboxylic acid derivatives of the formula I with X being NH$_2$, by heating compounds of formula II with a catalytical quantity of hydrogen halide in an alcohol ROH, in which R is defined as in formula I, and optionally further reacting said ω,ω-dialkoxycarboxylic acid derivatives of formula I with X being NH$_2$ by further heating them with a quantity of hydrogen halide, which is at least about equimolar, in the same alcohol ROH to yield ω,ω-dialkoxycarboxylic acid derivatives of the formula I with X being OR.

2. Process as claimed in claim 1, which comprises directly converting the ω-alkoxylactams of the formula II into ω,ω-dialkoxycarboxylic acid derivatives of the formula I with X being OR by heating them with a quantity of hydrogen halide at least about equimolar, in an alcohol ROH.

3. Process as claimed in claims 1 or 2, which comprises using methanol as the solvent ROH for reacting ω-alkoxylactams of the formula II with R being CH$_3$.

4. Process as claimed in claim 1 wherein the hydrogen halide is hydrogen chloride.

* * * * *